United States Patent
Mohs et al.

(10) Patent No.: US 11,617,804 B2
(45) Date of Patent: Apr. 4, 2023

(54) HYALURONIC ACID-BASED NANOPARTICLES AS BIOSENSORS FOR IMAGING-GUIDED SURGERY AND DRUG DELIVERY VEHICLES AND METHODS ASSOCIATED THEREWITH

(71) Applicant: Wake Forest University, Winston-Salem, NC (US)

(72) Inventors: Aaron Michael Mohs, Omaha, NE (US); Tanner Kinkade Hill, Omaha, NE (US); Sneha Sanjay Kelkar, York, PA (US); Steve Kridel, Clemmons, NC (US)

(73) Assignee: WAKE FOREST UNIVERSITY, Winston-Salem, NC (US)

( * ) Notice: Subject to any disclaimer, the term of this patent is extended or adjusted under 35 U.S.C. 154(b) by 0 days.

(21) Appl. No.: 15/326,694

(22) PCT Filed: Jul. 18, 2015

(86) PCT No.: PCT/US2015/041041
§ 371 (c)(1),
(2) Date: Jan. 17, 2017

(87) PCT Pub. No.: WO2016/011436
PCT Pub. Date: Jan. 21, 2016

(65) Prior Publication Data
US 2017/0202982 A1 Jul. 20, 2017

Related U.S. Application Data

(60) Provisional application No. 62/026,078, filed on Jul. 18, 2014.

(51) Int. Cl.
| | |
|---|---|
| A61K 49/00 | (2006.01) |
| G01N 33/574 | (2006.01) |
| G01N 33/58 | (2006.01) |
| G01N 33/543 | (2006.01) |
| A61B 5/00 | (2006.01) |
| A61B 10/00 | (2006.01) |
| A61K 31/337 | (2006.01) |
| B82Y 5/00 | (2011.01) |

(52) U.S. Cl.
CPC ........ *A61K 49/0093* (2013.01); *A61B 5/0075* (2013.01); *A61B 5/0086* (2013.01); *A61B 10/0041* (2013.01); *A61K 31/337* (2013.01); *A61K 49/005* (2013.01); *A61K 49/0034* (2013.01); *G01N 33/54346* (2013.01); *G01N 33/574* (2013.01); *G01N 33/582* (2013.01); *B82Y 5/00* (2013.01); *G01N 2400/40* (2013.01)

(58) Field of Classification Search
None
See application file for complete search history.

(56) References Cited

U.S. PATENT DOCUMENTS

| | | | |
|---|---|---|---|
| 2009/0004118 A1* | 1/2009 | Nie | A61K 49/0002 424/9.35 |
| 2011/0213121 A1 | 9/2011 | Kwon et al. | |
| 2014/0037542 A1 | 2/2014 | Bai et al. | |

FOREIGN PATENT DOCUMENTS

WO 2010131907 A2 11/2010

OTHER PUBLICATIONS

Choi et al (Self-assembled hyaluronic acid nanoparticles as a potential drug carrier for cancer therapy: Synthesis, characterization, and in vivo biodistribution. Journal of Materials Chemistry. Jun. 2009,19(24):4101-4107) (Year: 2009).*
Liu et al ( Biochemistry, molecular biology, and pharmacology of fatty acid synthase, an emerging therapeutic target and diagnosis/prognosis marker. Int J Biochem Mol Biol 2010;1(1):69-89) (Year: 2010).*
Ganesh et al (In Vivo Biodistribution of siRNA and Cisplatin Administered using CD44-Targeted Hyaluronic Acid Nanoparticles. J Control Release. Dec. 28, 2013; 172(3), p. 1-18) (Year: 2013).*
Lim et al (Self-assembled fluorescent magnetic nanoprobes for multimode-biomedical imaging. Biomaterials 31 (2010) 9310-9319) (Year: 2010).*
Liu et al., "Biochemistry, molecular biology, and pharmacology of fatty acid synthase, and emerging therapeutic target and diagnosis/prognosis marker," International Journal of Biochemistry and Molecular Biology (2010); 1(1): 69-89.
Hill et al., "Indocyanine Green-Loaded Nanoparticles for Image-Guided Tumor Surgery," Bioconjugate Chemistry (2015); 26(2): 294-303.

* cited by examiner

*Primary Examiner* — Jake M Vu
(74) *Attorney, Agent, or Firm* — Fox Rothschild LLP

(57) ABSTRACT

The present invention relates to intraoperative fluorescent imaging (IFI) used both pre-clinically using in-vivo models, as well as clinically to map sentinel lymph nodes in breast cancer, skin cancer, GI cancer, lung cancer, prostate cancer and several other cancers. IFI can be used to image solid tumors both non-specifically in hepatobiliary and breast cancers as well as in prostate and ovarian cancer. In one embodiment, two-dimensional resolution to 10 µm² is possible with optical imaging, significantly higher than other imaging modalities.
In one embodiment, the present invention relates to a series of self-assembled nanoparticles using HLA (hyaluronic acid) as both a polymeric backbone as well as targeting ligand. In some embodiments, the present invention relates to the synthesis of HLA conjugates, and the effect of variation of the hydrophobic ligand structure and conjugation level on nanoparticle self-assembly, size, ICG loading efficiency, and ICG fluorescence quenching and reactivation.

11 Claims, 10 Drawing Sheets

HYALURONIC ACID-BASED NANOPARTICLES AS BIOSENSORS FOR IMAGING-GUIDED SURGERY AND DRUG DELIVERY VEHICLES AND METHODS ASSOCIATED THEREWITH

This application claims priority under 35 USC 119(e) to U.S. Provisional Application No. 62/026,078, filed Jul. 18, 2014, the entire contents of which are incorporated by reference in its entirety.

Some aspects of this invention as described in this application were sponsored by NIH R00CA153916. Accordingly, the Federal Government has rights in this application.

BACKGROUND OF THE INVENTION

Surgery is used as the primary treatment for most solid tumors. For example, 70-80% of breast, colorectal, lung, and bladder cancer patients receive surgery to treat their disease. Complete tumor removal, including other local malignancies and metastatic lymph nodes is the most importance factor for complete disease remission. The importance of a complete surgical resection is striking: patients who have a complete tumor resection have a 3 to 5-fold improvement in survival compared to patients with incomplete resection.

Directly related to tumor recurrence is the presence of positive surgical margins (SM), i.e. tumor deposits at the border of excised tissue. For example, pSMs in after breast conserving surgery leads to higher rates of local recurrence, increasing the potential for systemic disease and patient death. Generally, more than 20% of breast tumor resections require re-exision. Regarding prostate cancer, the overall incidence of pSMs is 15%, which has not improved in decades. pSMs are associated with an almost 4-fold higher risk of progression and decreased biochemical recurrence free survival. Recurrent prostate cancer can lead to further intervention, including additional surgery, salvage radiation therapy, and androgen deprivation therapy. Furthermore, in patients with colon cancer, treatment by a combination of chemotherapy and surgery indicated that pSMs were the primary risk factor for patient survival. Regardless of the tumor type, additional therapies exact a cost to patients financially, psychologically, and impose additional medical risks—each decrease quality of life.

A contributing factor to high tumor recurrence is due to limited techniques that intraoperatively evaluate SMs in their entirety, or the cavity where the tumor was removed. The current gold standard for tumor margin status is immunohistochemistry (IHC), which may not provide definitive information for days after surgery. A surgeon relies upon his/her eyes, hand, and experience to remove tumor(s), but this process is subjective. Complicating complete removal of tumor is competing criterion on how to take tumor margins intraoperatively. For example, it is speculated that increasing the threshold distance for declaring negative margins leads to a decrease in local recurrence, while others have postulated that increasing margin width may not be appropriate in all tumors.

Complete treatment of the various cancers is important. In the United States, over 200,000 cases and nearly 40,000 deaths are expected to result each year from invasive breast cancer. In addition to radiation and chemotherapy many of these cases are treated surgically using mastectomy or breast conserving surgery. Of those patients treated surgically approximately 30%/o will experience a recurrence of disease either locally or systemically, making it critical to ensure efficient and complete removal of positive tumor margins and local metastases to prevent local recurrence and formation distant metastases. Current methods of tumor resection primarily involve palpation and visual inspection, which provide poor visual contrast, resolution, and specificity. With the angiogenic switch of tumors occurring before they reach 1 mm in diameter, a more effective means of establishing tumor boundaries, local metastases, and sentinel lymph nodes is needed.

Moreover, surgery is the primary course of treatment for men with prostate cancer (CaP). Complete removal of all cancerous tissue during radical prostatectomy (RP), negative surgical margins (SM), is associated with lower recurrence. Despite improved preoperative imaging, minimally-invasive techniques, anesthesia, etc., the tumor recurrence rate remains high for prostate cancer. In one study, 100 consecutive RPs were performed wherein the surgeon recorded intraoperatively whether he thought the tumor extended into the SM. The surgeon decided in all 100 cases that the margins were negative; but pathology showed positive SMs in 39 patients. Overall, the incidence of positive SMs after RP is 5%-43%, which can have a dramatic impact on patient prognosis.

Current imaging modalities used for cancer include x-ray, MRI, PET, SPECT, and ultrasound, but unfortunately these modalities either involve instrumentation that is too cumbersome to use in the operating room or are incapable of providing tumor specific information with high resolution. Moreover, conventional imaging techniques, such as magnetic resonance imaging (MRI) and ultrasound (US), have been used for intraoperative imaging. However, MRI is expensive and requires use of specialized non-magnetic surgical instruments. US is useful in guiding interventional procedures, but cannot depict pSMs due to poor resolution and sensitivity.

Providing surgeons with real-time information on the location of cancerous tissue, as is obtained by imaging, would decrease medical costs from additional procedures and ongoing treatment, assist doctors and hospitals in ensuring the best treatment, and ultimately improve patient outcomes. Near infrared (NIR) imaging utilizes wavelengths in the range of 700-900 nm and is of particular interest as this range has very low autofluorescence from surrounding tissue and excellent tissue penetration, allowing for high signal to background ratio (SBR) and imaging up to several millimeters into the tissue. Several NIR imaging modalities are already available commercially or have been examined clinically. Indocyanine green (ICG) is currently the only fluorophore, which both absorbs and fluoresces well into the NIR range and is approved by the FDA. ICG has previously been used clinically for image guided surgery in a number of capacities, including sentinel lymph node mapping, solid tumor removal, and angiography. However, when ICG is administered systemically it associates almost exclusively with serum albumin and other serum proteins and thus is not targeted specifically to tumors. In order to specifically label tumors with ICG, it would be desired to conjugate ICG to a targeting ligand or antibody. Thus, a more effective and contemporaneous means of establishing tumor boundaries, local metastases, and sentinel lymph nodes is needed.

Many cancer types overexpress CD44, one of the main cell surface receptors for hyaluronic acid (HLA). HLA is one of the major components of the extracellular matrix, found throughout the body but particularly in soft connective tissue. This overexpression, in combination with the common overexpression of hyaluronidases, enzymes that cleave HLA, may allow for both specific targeting to, and activation within, tumors. It has been suggested that hyaluronidase, in particular HYAL-1, is associated with increasing tumor grade and metastasis. HYAL-1 degrades the polysaccharide HLA in tumor extracellular matrix (ECM). Therefore, NPs composed of HLA would specifically degrade in the presence of HYAL-1.

Improved surgical detection of CaP would have a significant impact on tumor recurrence and the psychological burden associated with an incomplete tumor resection. It would be desirable to target optical imaging agents at proteins that are known to be involved in the CaP invasion process; which would "highlight" cells most likely to be missed during surgery. To that end, the role of hyaluronic acid (HLA) and hyaluronidase in CaP progression could provide the molecular pathways for improved surgical CaP detection and resection.

BRIEF SUMMARY OF THE INVENTION

In one embodiment, intraoperative fluorescent imaging (IFI) can successfully be used both pre-clinically using in-vivo models, as well as clinically to map sentinel lymph nodes in breast cancer, skin cancer, GI cancer, lung cancer, prostate cancer and several other cancers. IFI can be used to image solid tumors both non-specifically in hepatobiliary and breast cancers as well as in prostate and ovarian cancer. As opposed to modalities such as MRI and SPECT, instrumentation required for IFI need be no larger than a pen-sized laser with an overhead camera system to view the surgical field and a display. Additionally, two-dimensional resolution of 10 $\mu m^2$ is possible with optical imaging, significantly higher than other imaging modalities.

Accordingly, the present invention relates to a series of self-assembled nanoparticles using HLA as both a polymeric backbone as well as targeting ligand. In embodiments, the present invention relates to the synthesis of HLA conjugates, and the effect of variation of the hydrophobic ligand structure and conjugation level on nanoparticle self-assembly, size, ICG loading efficiency, and ICG fluorescence quenching and reactivation.

In order to label tumors with ICG one may conjugate ICG to a targeting ligand or antibody, and in the present invention, load ICG into ligand-containing nanoparticles (NPs).

In one embodiment, the present invention relates to NP uptake into CD44-expressing cancer cells as well as ICG delivery to solid tumors.

DETAILED DESCRIPTION OF THE INVENTION

Figure 1:
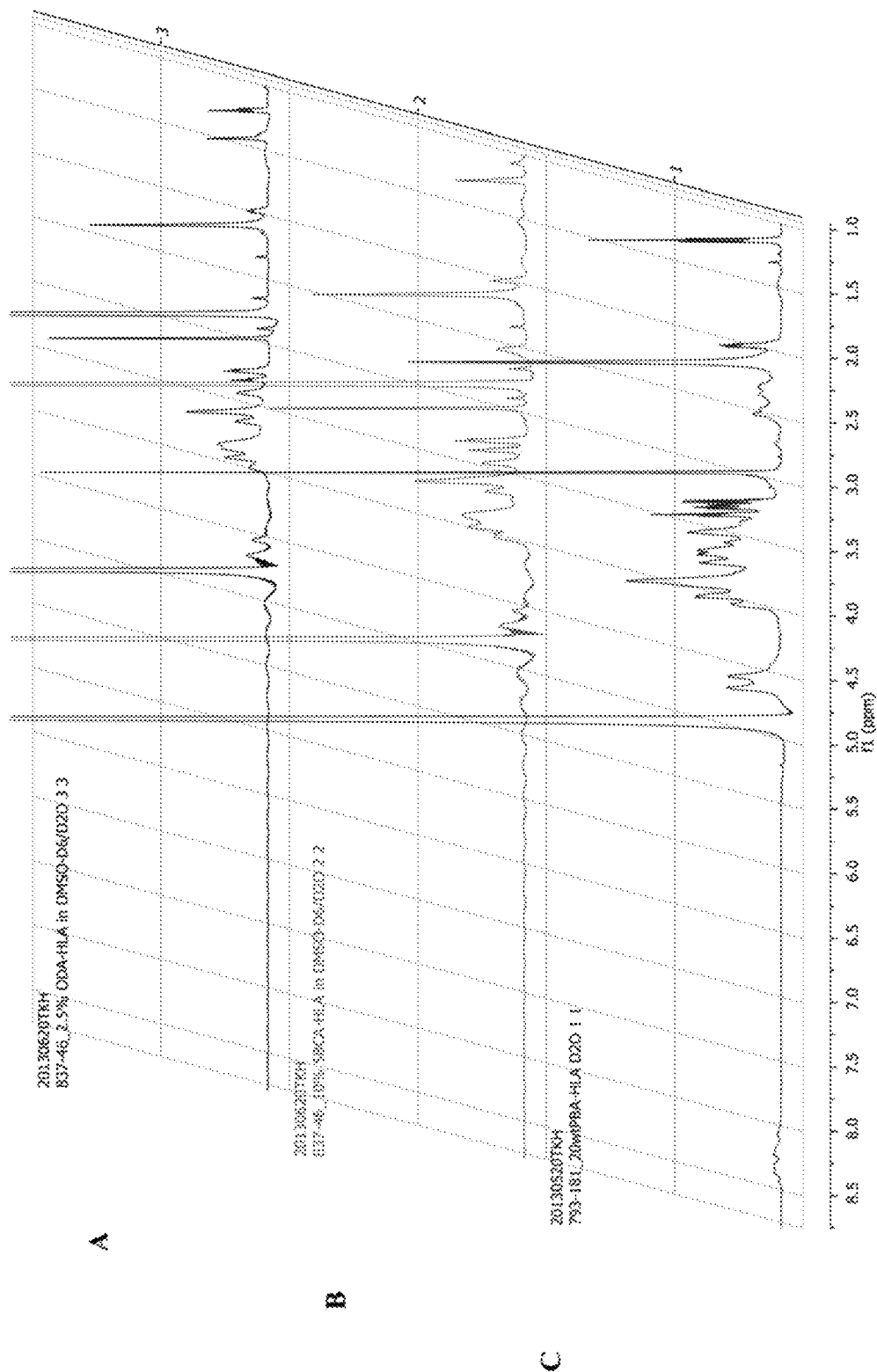
FIG. 1 shows NMR spectra of hydrophobic ligands conjugated to HLA. (A) shows 2.3 wt % ODA-HLA. (B) shows 3.33 wt % 5-βCA-HLA. (C) shows 11 wt % PBA-HLA.

The present invention relates to the use of optical imaging, which has unique advantages for image-guided surgery (IGS) and detection of pSMs. In the near infrared (NIR) spectrum, standard fiber optics and silicon-based CCD cameras can be used for tumor visualization at high sensitivity and low costs. Systems in the NIR are optimal for imaging contrast agents because at 700-1000 nm background autofluorescence and scattering from native tissue is minimal. In an embodiment, the present invention relates to several optical imaging systems based on detecting contrast-enhanced fluorescence emission. In an embodiment, the optical contrast agents that are part of the present invention can detect tumor tissue with high sensitivity and specificity, which are vital for successful intraoperative imaging.

The present invention also relates to a series of self-assembled nanoparticles using HLA (hyaluronic acid, i.e., hyaluronan) and its derivatives as both a polymeric backbone as well as targeting ligand(s). In embodiments, the present invention relates to the synthesis of HLA conjugates, and the effect of variation of the hydrophobic ligand structure and conjugation level on nanoparticle self-assembly, size, ICG (indocyanine green) loading efficiency, and ICG fluorescence quenching and reactivation.

In order to label tumors with ICG, one may conjugate ICG to a targeting ligand or antibody, and in the present invention, load ICG into ligand-containing nanoparticles (NPs).

In one embodiment, the present invention relates to NP uptake into CD44-expressing cancer cells as well as ICG delivery to solid tumors.

In one embodiment, some NIR (near infrared) fluorophores can be quenched in NPs (nanoparticles) and activated upon NP degradation. Thus, in one embodiment, the present invention relates to using HYAL-1 (hyaluronidase-1) to activate NIR fluorescent dyes in the CaP (prostate cancer) ECM (extracellular matrix). The activated fluorophores can then be detected in NIR optical imaging systems for image-guided surgery (IGS). It should be noted that NIR-labeled HLA will likely be useful because up to 60% of prostate primary tumors overexpress CD44, the natural receptor for HLA.

In another embodiment, the presence of HYAL-1 in CaP ECM and HLA degradation by HYAL-1 render HLA-based NPs an ideal vehicle to deliver therapeutics to prostate tumors. In one embodiment, Orlistat, which has been shown to be FAS inhibitors, may be used to treat and or prevent the progression of prostate cancer. HLA-based NPs will likely provide an ideal drug delivery system that could preferentially deliver Orlistat to prostate tumors, and then degrade in the ECM due to HYAL-1; the degradation would release Orlistat to transport into CaP cells. Fluorescence labeling of the NP would combine neoadjuvant chemotherapy with IGS to further improve surgical outcomes.

Thus, in one embodiment, the present invention relates to using intraoperative imaging agents that fluorescently contrast-enhance CaP during surgery by image-guided surgical instrumentation giving surgeons/urologist more effective visualization of prostate cancer, thereby increasing the probability of complete tumor removal.

In an embodiment, the present invention relates to fluorescent HLA-based NPs that entrap fatty acid synthase (FAS) inhibitors, such as Orlistat, which will allow them (and Orlistat) to be specifically delivered in CaP for neoadjuvant therapy to image-guided surgery.

Results and Discussion

FIG. 1 shows NMR spectra of hydrophobic ligands conjugated to HLA wherein (A) shows 2.3 wt % ODA-HLA, (B) shows 3.33 wt % 5-CA-HLA, (C) shows 1 wt % PBA-HLA. Some impurities are present between 3-3.5 ppm, which are likely residual products of the EDC/NHS reaction.

ICG loading was examined using NMR. Suspension of NPs in $D_2O$ did not allow for observation of the ICG peak, likely because when associated with the NPs ICG is in a semi-solid state which prevents acquisition of the signal. Upon dissolution into 50/50 DMSO-$D_6$/$D_2O$ the ICG peak becomes apparent (FIG. 2).

Figure 2:
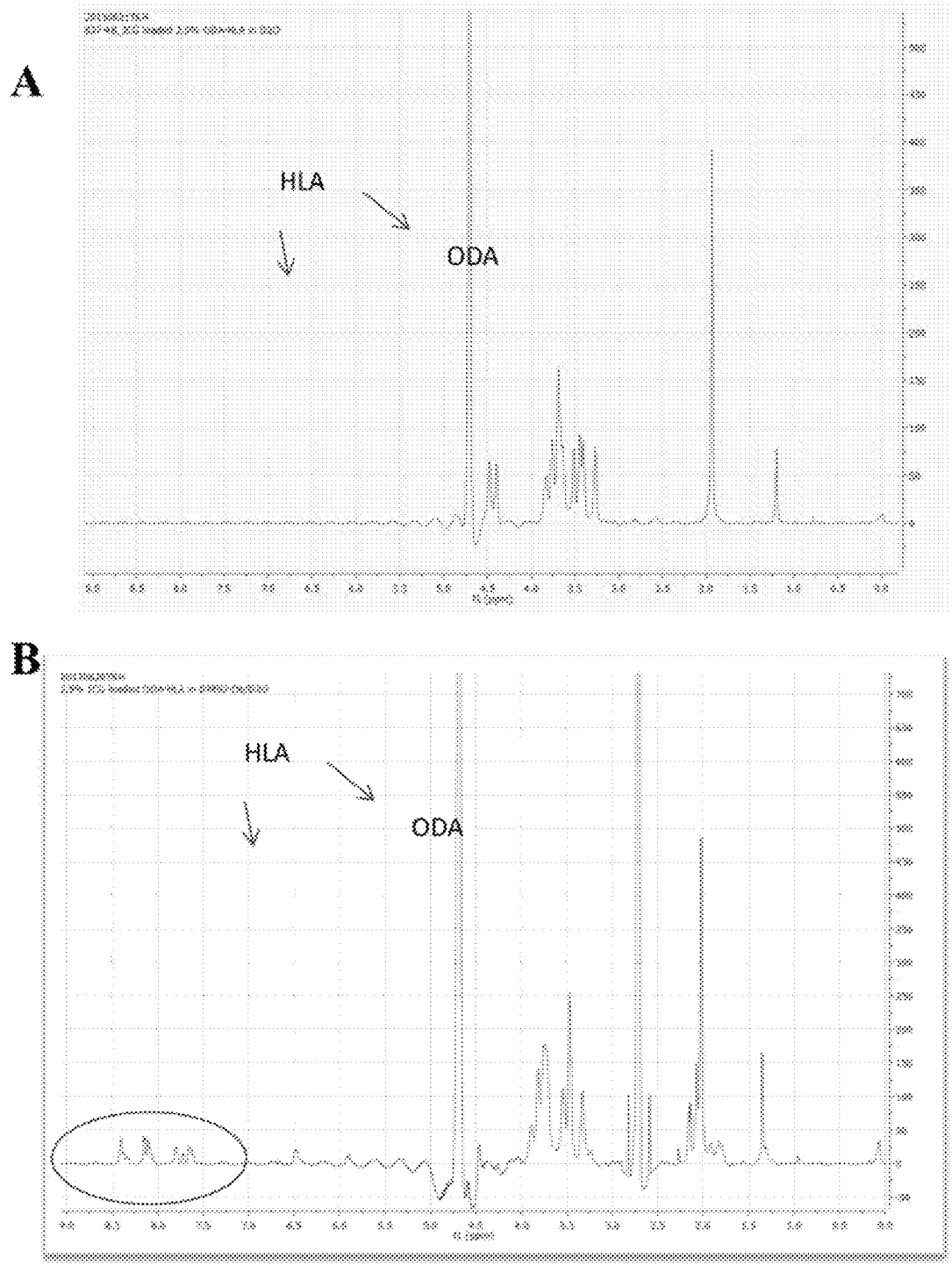
FIG. 2 shows A: ICG-loaded 2.5 wt % ODA-HLA NPs in $D_2O$, note absence of C=C peaks. B: the same sample as (A) mixed in 50/50 DMSO-$D_6$/$D_2O$, showing C=C peaks indicative of ICG.

FIG. 2 A: shows ICG-loaded 2.5 wt % ODA-HLA NPs in $D_2O$. Note the absence of C=C peaks. B: shows the same sample as (A) mixed in 50/50 DMSO-$D_6$/$D_2O$, showing C=C peaks indicative of ICG.

Nanoparticles were characterized using DLS, UV-Vis, and fluorescence spectroscopy. UV-Vis spectroscopy showed a strong scattering signal around the ICG peak when NPs were dissolved in pure water, suggesting the ICG was associated with the NPs. Upon dissolution into DMSO/$H_2O$ the ICG peak took on it's usual shape, suggesting the NPs had disassembled and released ICG into solution (FIG. 3).

Figure 3:
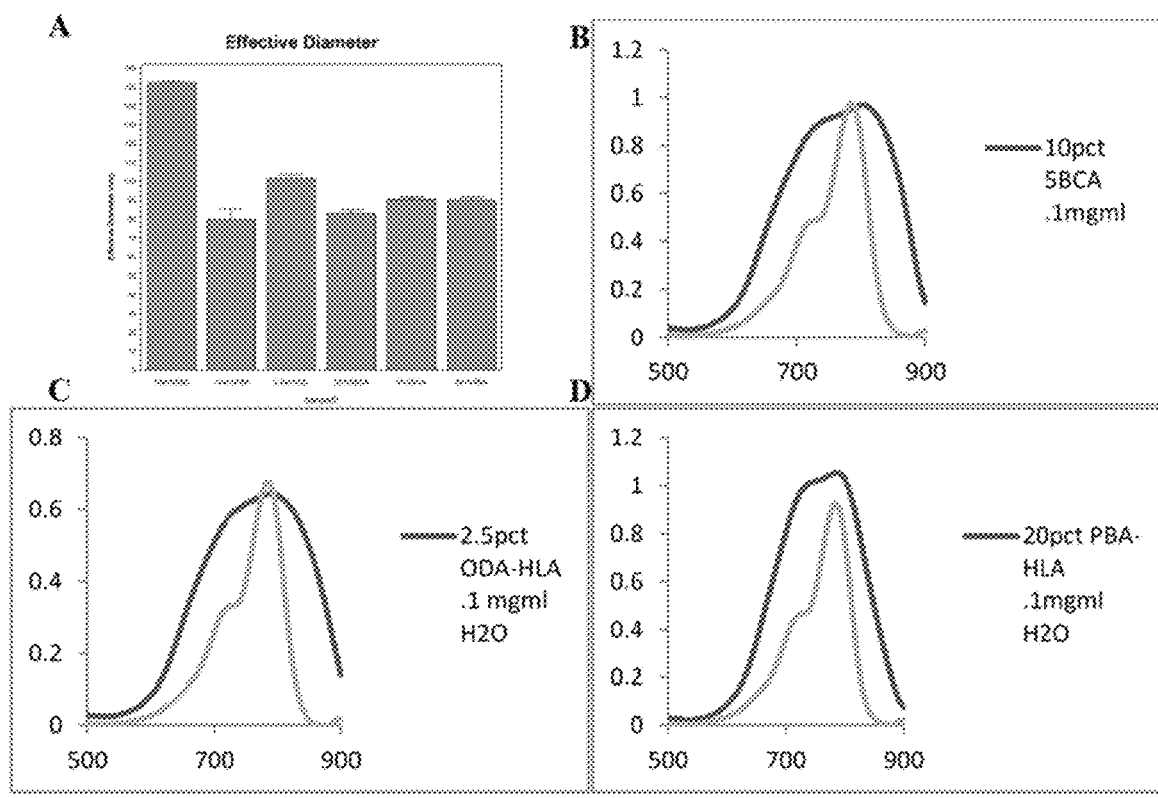
FIG. 3 shows effective diameters of all NPs were less than 160 nm prior to ICG loading (A). Absorbance spectroscopy showed a broad scattering peak between 600-900 nm when ICG-NP material was dissolved in pure $H_2O$ (B-D). Mixing with DMSO eliminated the broad peak and saw the return of the characteristic ICG absorption spectrum.

FIG. 3. The effective diameters of all NPs were less than 160 nm prior to ICG loading (A). Absorbance spectroscopy showed a broad scattering peak between 600-900 nm when ICG-NP material was dissolved in pure H2O (B-D). Mixing with DMSO eliminated the broad peak and saw the return of the characteristic ICG absorption spectrum.

Figure 4:
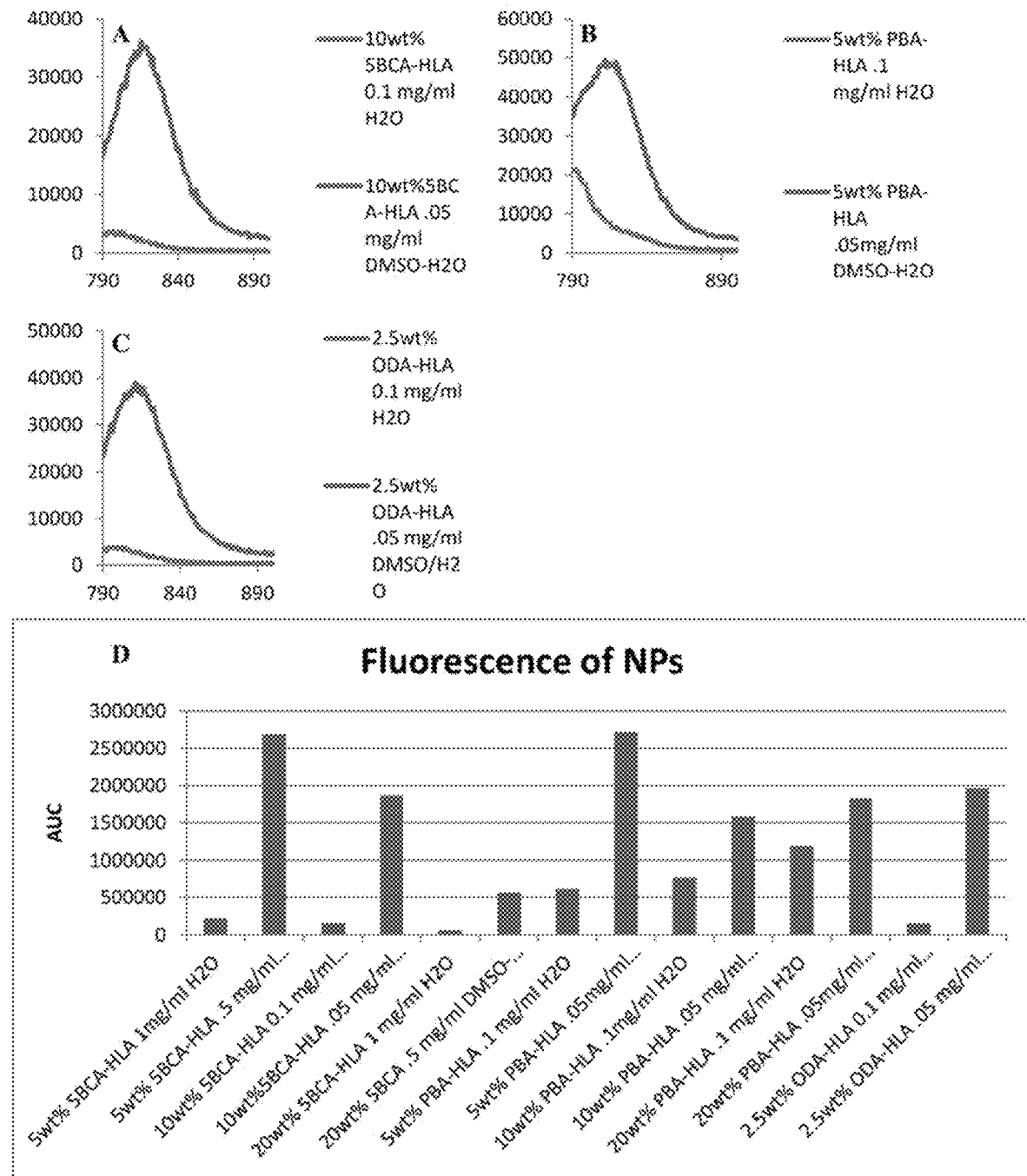
FIG. 4 shows (A-C) Fluorescence quenching of ICG-loaded NPs in pure water (blue line) and fluorescence reactivation when dissolved in 50/50 DMSO/$H_2O$ (red line). (D) Quantification using area under the curve (AUC) of fluorescence spectra for all NPs tested.

ICG fluorescence in NPs was quenched in when NPs formed in pure water or PBS, but could be reactivated by dissolving in 50/50 DMSO/$H_2O$ (FIG. 4). All NPs investigated showed this quenching and reactivation, though the extent of reactivation may be dependent on the ICG loading efficiency.

FIG. 4. (A-C) Fluorescence quenching of ICG-loaded NPs in pure water (blue line) and fluorescence reactivation when dissolved in 50/50 DMSO/H2O (red line). (D) Quantification using area under the curve (AUC) of fluorescence spectra for all NPs tested.

Fluorescence resulting from ICG uptake into CD44 expressing MDA-MB-231 cells was found after a 24 hour incubation in the presence of ICG-loaded 5% PBA-HLA NPs, suggesting that NP facilitated delivery to CD44 expressing tumors would be feasible. Cytotoxicity of the NPs appeared negligible when using ICG-loaded NPs, though toxicity was observed at higher concentrations of NPs without ICG. This may result from a stabilizing effect that ICG has on NP structure which prevents NP material from interacting with the lipid bilayer. It should also be noted that 0.5-1 mg/ml is a significantly higher concentration than would ever be experienced in vow.

Figure 5:
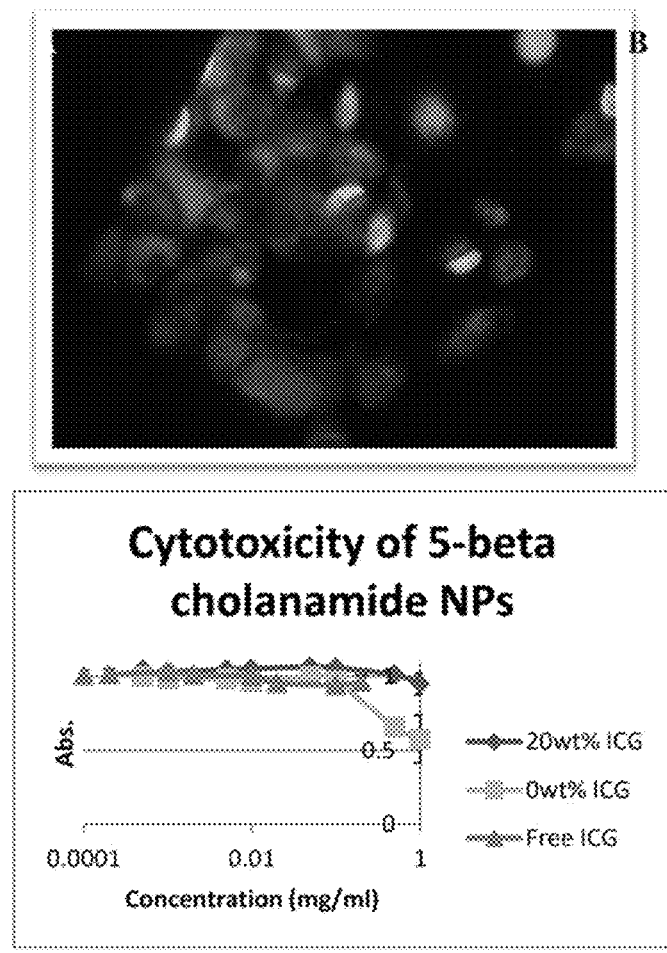
FIG. 5 shows (A) MDA-MB-231 cells incubated for 24 hours in 1 mg/ml NPs. Blue shows DAPI staining, red is false coloring of ICG. (B) Cytotoxicity of MDA-MB-231 cells incubated for 24 hours in the presence of NPs with or without ICG, or ICG alone.
Figure 6:
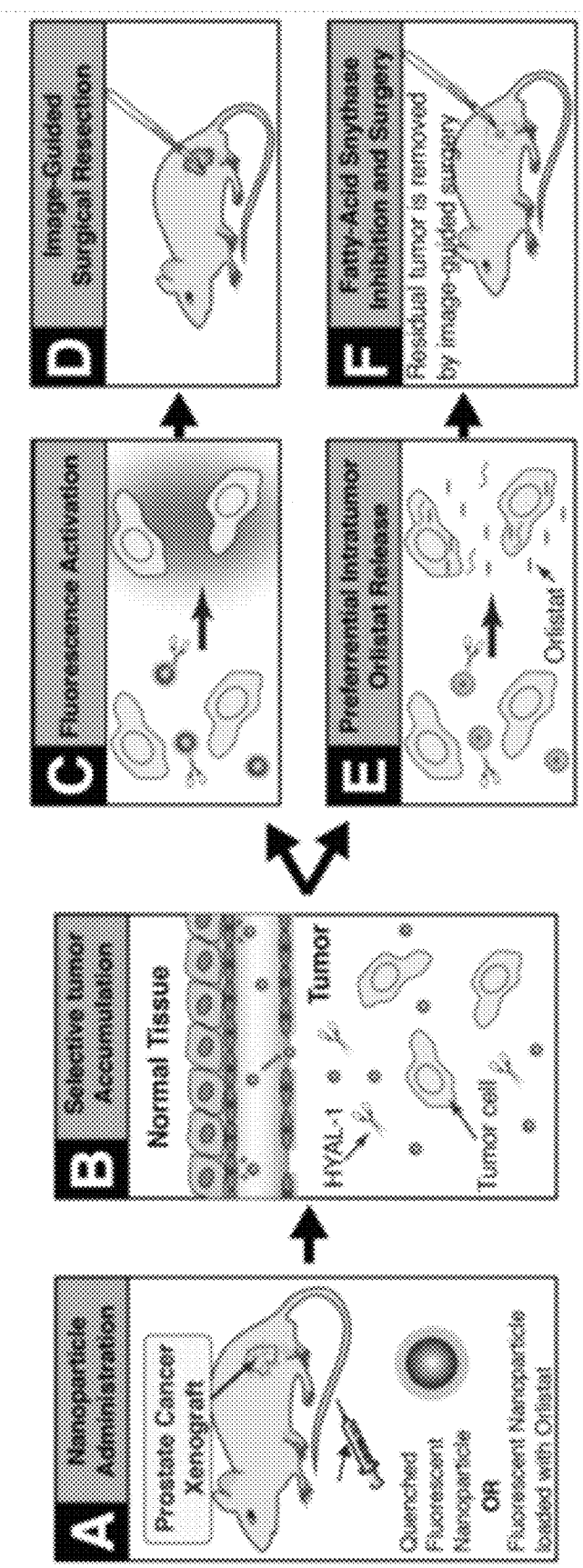
FIG. 6 shows Nanoparticles will be systemically injected (A) and selectively accumulate in tumor tissue (B). The nanoparticles have fluorescence that specifically activates due to HYAL-1 in CaP tumor microenvironment (C), providing clear definition of tumor margins (D). Systemically injected multifunctional composition will deliver Orlistat for tumor inhibition (E) and a fluorophore for IGS (F) to evaluate the combined role of chemotherapy and IGS to treat CaP.
Figure 7:
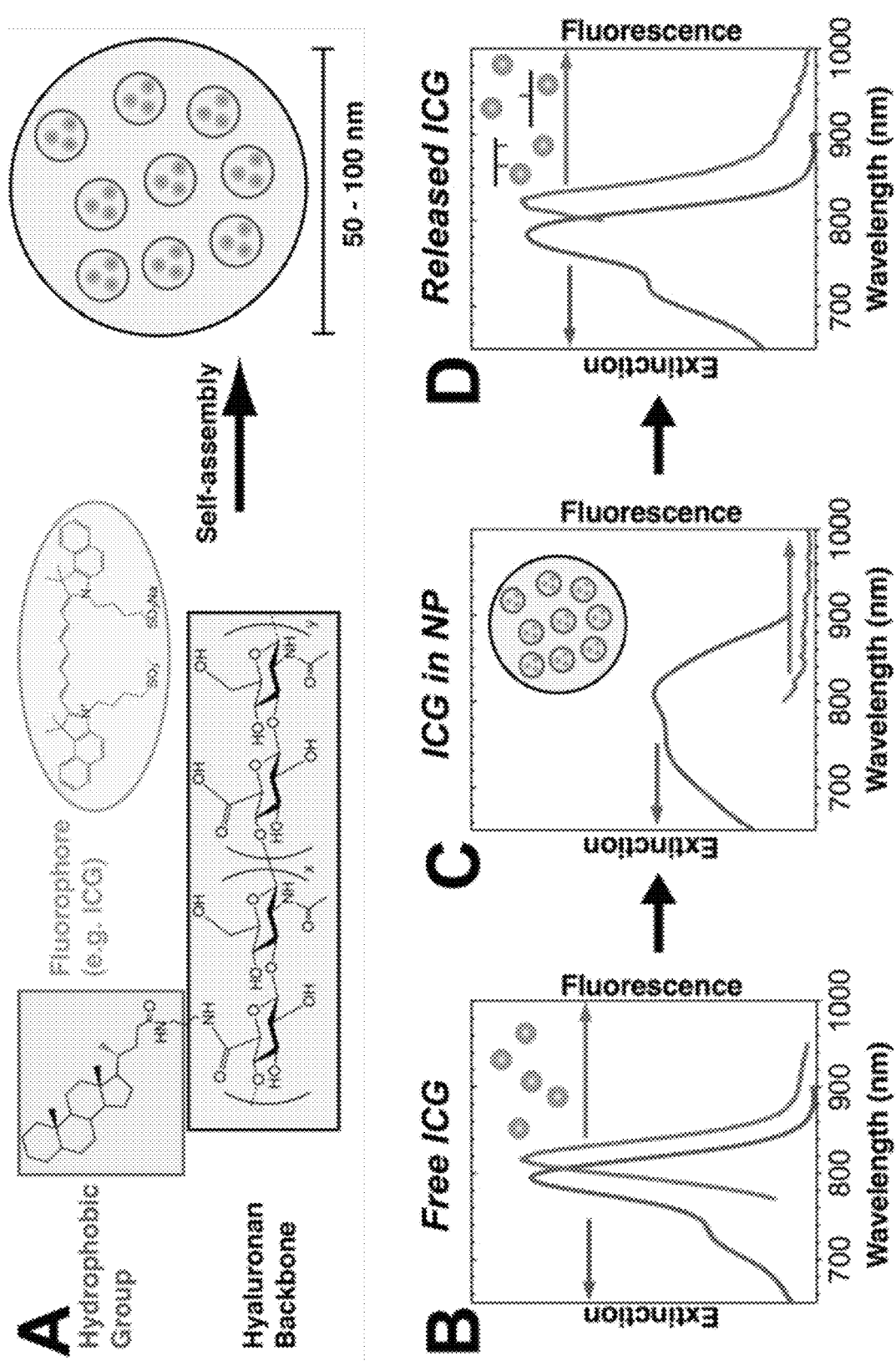
FIG. 7 shows (A) the HLA conjugates self-assembles with ICG in aqueous conditions to entrap ICG within hydrophobic pockets in the resultant self-assembled fHNP (fluorescent Hyaluronan-based nanoparticles, also known as dye loaded nanoparticles). (B) shows Free ICG has strong NIR absorbance and fluorescence. (C) shows entrapping ICG in a nanoparticle broadens extinction spectra and quenches fluorescence emission. (D) shows upon release from nanoparticle, the strong NIR absorbance and emission is regained.
Figure 8:
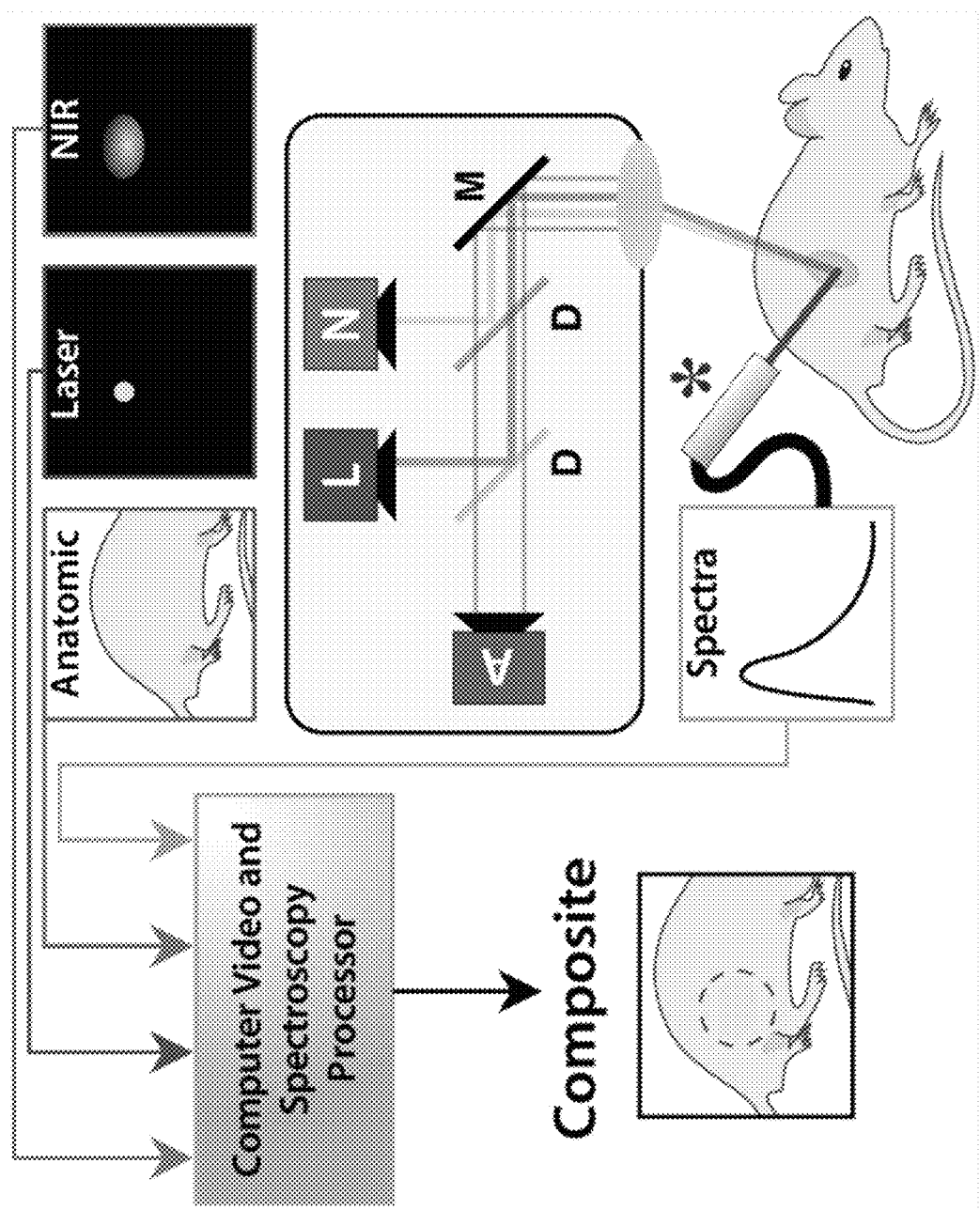
FIG. 8 shows the Design and Detection of ICG. The fluorescence image-guided surgical system method uses a widefield imaging head that is positioned over the area of interest and uses a directed laser excitation source (*). Area imaging requires 3 cameras to monitor the anatomical view (A), the laser position (L), and any NIR fluorescence emission (N). The area is imaged by a common objective lens and folded by mirrors (M) and by dichroic mirrors (D).

FIG. 5. (A) MDA-MB-231 cells incubated for 24 hours in 1 mg/ml NPs. Blue shows DAPI staining, red is false coloring of ICG. (B) Cytotoxicity of MDA-MB-231 cells incubated for 24 hours in the presence of NPs with or without ICG, or ICG alone. ICG appear to decrease NP toxicity, possibly due to hydrophobic stabilizing effect.

Mass spectra of the intermediate methyl-ester products were taken to confirm their presence. Synthesis of the amide products by reflux in diaminopropane yielded the final products shown (Scheme 1A). Mass spectra and NMR spectra of these products were also taken to confirm their identities. Conjugation of the hydrophobic amides or octadecylamine to the carboxylate group on glucuronate was facilitated with an EDC/NHS reaction as shown in Scheme 1B.

Scheme 1.

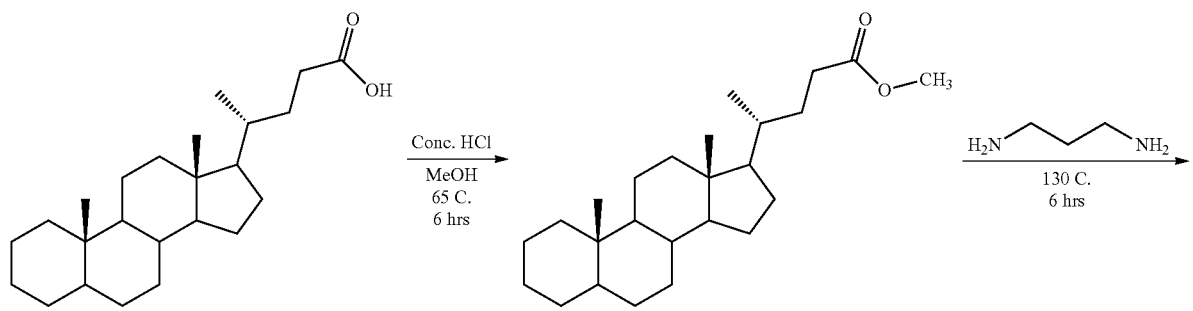

A

-continued
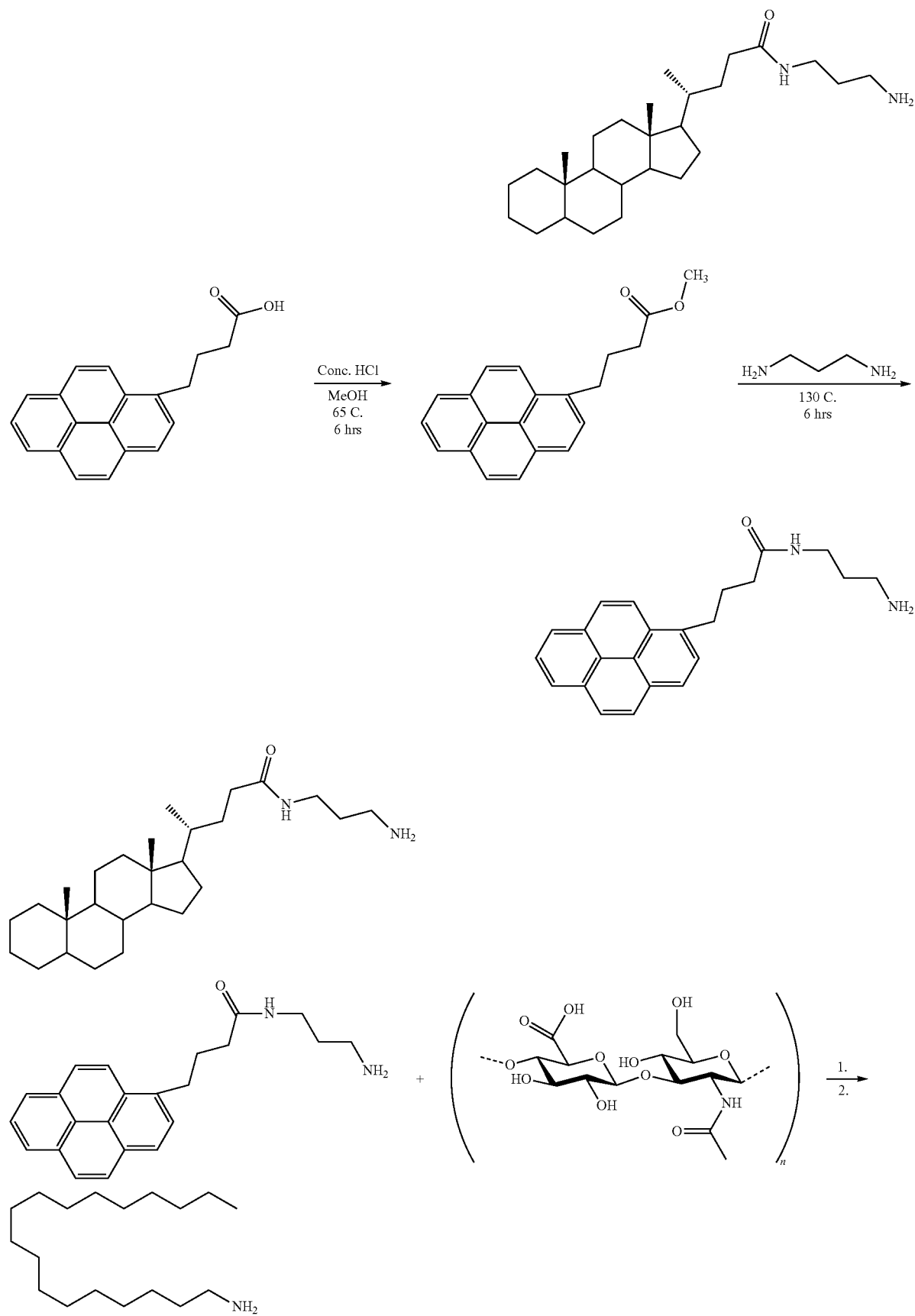

-continued

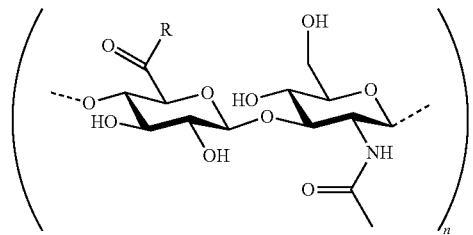

A: Synthesis of hydrophobic amides using 5-β cholanic acid 1-pyrenebutyric acid.
B: Conjugation of hydrophobic ligands to HLA.
1. Reactions conditions: EDC/NHS in 50/50 DMF/H2O for 24 hours used for 5-βCA-HLA or PBA-HLA conjugation.
2. Reaction conditions: EDC/NHS in 70/30 ethanol/H2O for 24 hours used for octadecylamine-HLA conjugation.

Scheme 2 shows the synthesis of amphiphilic hyaluronic acid. 5-β-cholanic acid and 1-pyrenebutyric acid were converted to primary amines with diaminopropane. Conjugation with the primary amines of the hydrophobic ligands was achieved using NHS/EDC coupling chemistry.

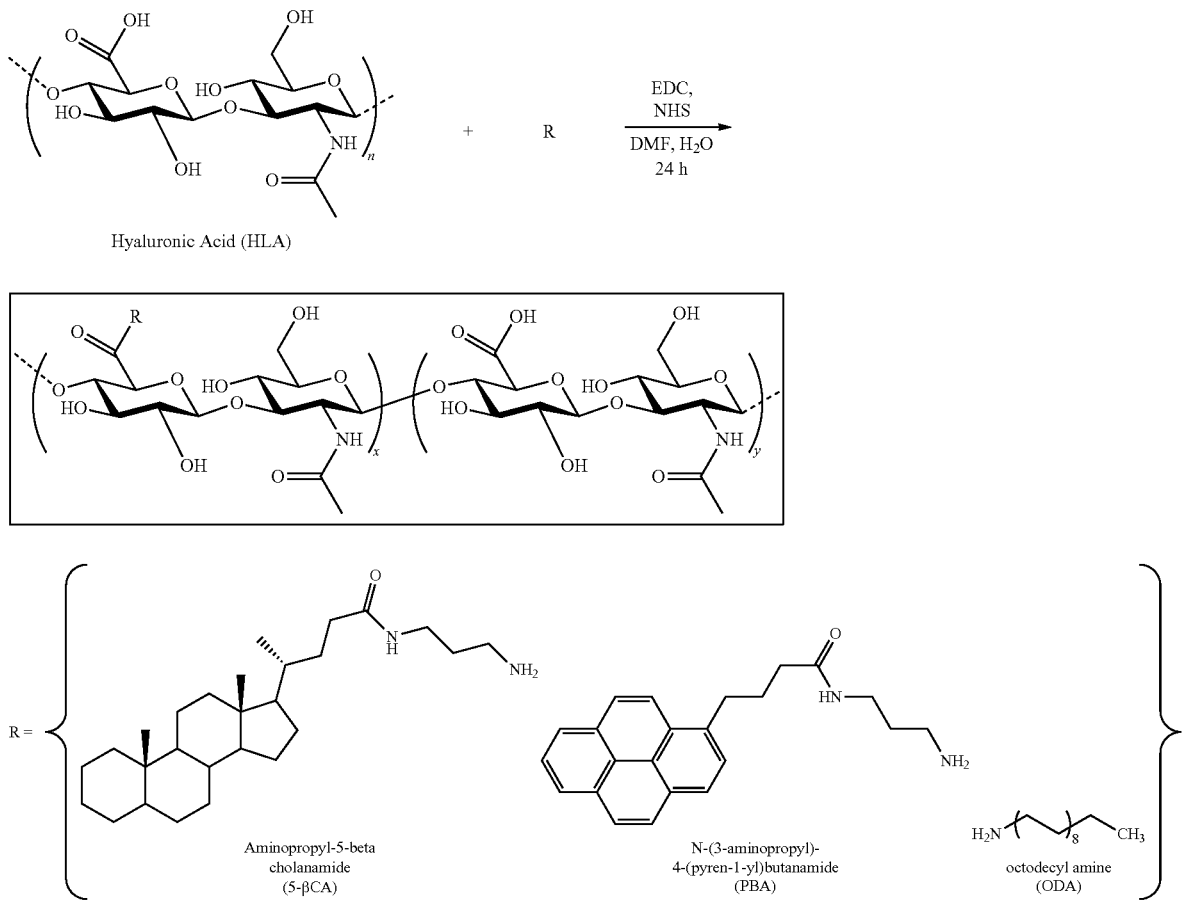

Conjugation of the hydrophobic ligands to HLA was performed using multiple loading ratios of 5 wt %, 10 wt %, and 20 wt % for 5-β cholanamide-HLA (5-βCA-HLA) and pyrenebutanamide-HLA (PBA-HLA), and 2.5 wt % for octadecylamine-ODA. Successful conjugation was observed for all products in the NMR spectra (See FIG. 1). This synthesis provided amphiphilic HLA polymers with varying degrees of substitution of hydrophobic ligands necessary to drive self-assembly and provide a hydrophobic core for accumulation of ICG. Actual conjugation efficiencies and ICG loading efficiencies are shown in Table 1.

TABLE 1

Characterization and ICG loading of HLA conjugates

| Sample[a] | Loading %[b] | Actual %[c] | Diameter ±SD NP (ICG+) | Diameter ± SD NP (ICG−) | ICG loading efficiency[d] |
|---|---|---|---|---|---|
| 5% 5-βCA-HLA | 4.8 | | 90.61 ± 1.04 | 150.88 ± 8.64 | .060 |
| 10% 5-βCA-HLA | 10.1 | 6.0 | 152.24 ± .78 | 258.11 ± 4.59 | .475 |
| 5% PBA-HLA | 5.8 | 5.67 | 90.17 ± 1.06 | | .501 |
| 10% PBA-HLA | 12.2 | 10.1 | 79.72 ± 5.62 | 154.87 ± 2.04 | .470 |
| 2.5% ODA-HLA | 2.8 | 2.77 | 101.58 ± 1.90 | 163.91 ± 20.86 | .327 |

[a]Sample identification.
[b]Molar loading ratio.
[c]Observed molar loading ratio calculated from NMR integration.
[d](Observed ICG concentration measured by UV-vis)/(Theoretical concentration)

Three structurally distinct hydrophobic moieties were examined to determine their effect on driving self-assembly and ICG loading. 5-β cholanic acid, a cholesterol-like moiety, was chosen which was previously seen to successfully drive self-assembly, as well as load and deliver a chemotherapeutic drug camptothecin. The polycyclic aromatic compound 1-pyrenebutyric acid was studied as well as the linear hydrocarbon octadecylamine (ODA). The hydrophobic ligands aminopropyl-5-β cholanamide (5-βCA) and aminopropyl-1-pyrenebutanamide (PBA) were synthesized by first converting the compounds to a methyl ester and then by addition of diaminopropane to give a primary amine for conjugation to the carboxylate group on HLA, while ODA was conjugated without modification. It was thought that 5-βCA and PBA would provide a more sterically favorable hydrophobic environment for ICG and thereby increase loading efficiency, with PBA in particular having the potential for π-π stacking with ICG. As ODA is not sterically similar to ICG but is capable of efficient self-association it was thought that ODA would load ICG less efficiently than either 5-βCA-HLA or 5-βCA-HLA.

Figure 9:
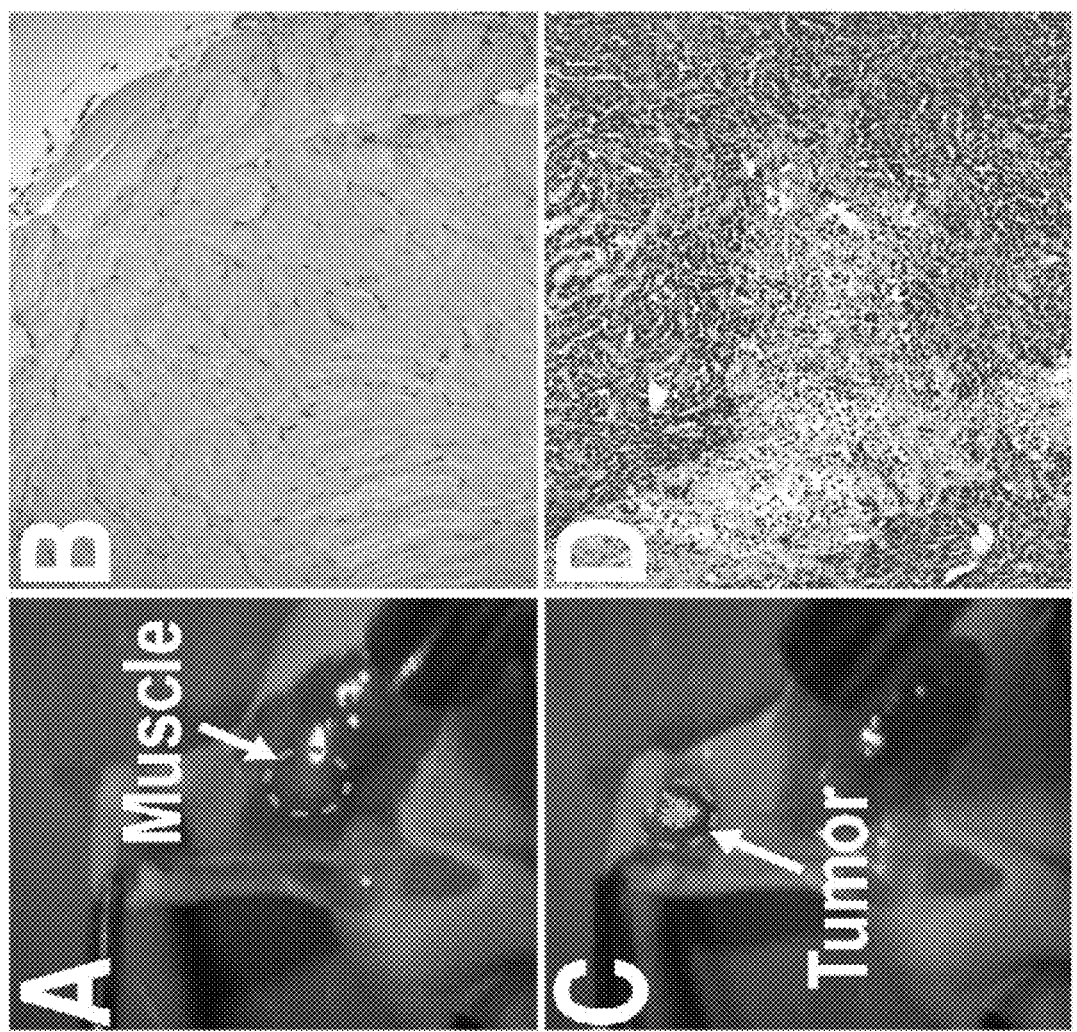
FIG. 9 shows ICG detection in tumors using the fluorescence image-guided surgical system method. (A) Excitation light directed at muscle results in no enhancement and is (B) confirmed by pathology. (C) Excitation at tumor shows strong NIR enhancement due to ICG and is confirmed to be tumor (D).
Figure 10:
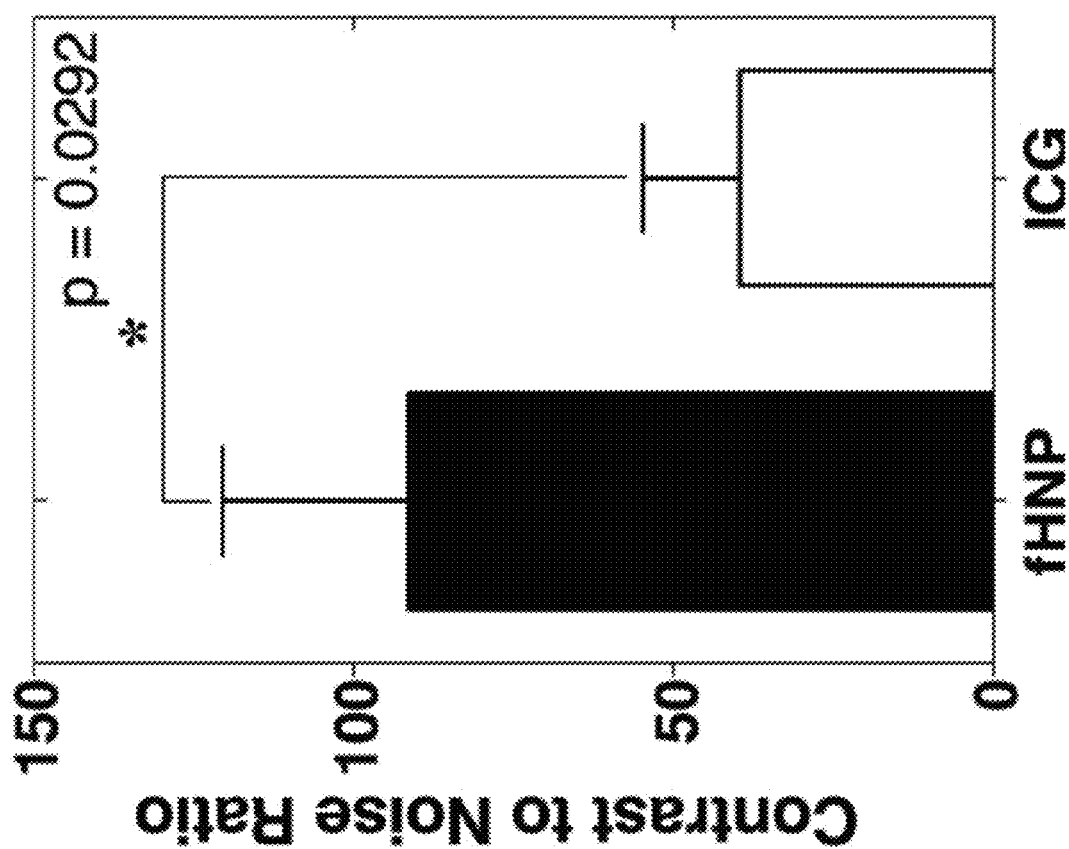
FIG. 10 shows that I.V. injection of 10 nmol of ICG (free or fHNP) results in tumor signal enhancement. The tumor signal after necropsy reveals fHNPs result in a significantly higher CNR (Contrast to Noise Ratio).

FIG. 9 demonstrates the capability of the fluorescence image-guided surgical system method in a mouse bearing an ectopic 4T1 breast tumor. In this experiment, 0.357 mg/kg ICG was systemically administered via a tail vein. After 24 hours, the mouse was euthanized and tumor fluorescence enhancement was assessed by using the fluorescence image-guided surgical system method. When the laser excitation source of fluorescence image-guided surgical system method is directed off the tumor (FIG. 9A,B), no fluorescence enhancement of the tumor is seen. FIG. 9C,D shows that when the fluorescence image-guided surgical system method laser excitation source is directed at the tumor, strong fluorescence signal is seen due to ICG. This example uses a breast tumor model.

Materials and Methods

5-Beta Cholanamide Synthesis 2.8 mmol of 5-beta cholanic acid was dissolved into 5 ml methanol. 180 ul of concentrated HCl was added and this solution was refluxed at 60-65 C for 6 hours. The product was cooled to 0 C to obtain a white precipitate. The precipitate was vacuum filtered and washed with cold methanol, then dried under vacuum. This product is the 5-beta cholanic methyl ester. 5-beta cholanic methyl ester was then dissolved into 300 mmol 1,3 diaminopropane and refluxed at 130 C for 6 hours. The solution was then cooled to 0 C and crystallization of the product was forced by addition of nanopure water. The white precipitate was then washed with 200 ml cold nanopure water under vacuum filtration and dried under vacuum. This product is aminopropyl 5-beta cholanamide (5BCA).

1-Pyrenebutanamide Synthesis

Dissolved 557 mg 1-pyrenebutyric acid (Sigma Aldrich) into 5.5 mil MeOH with 180 ul 37% HCl. This solution was refluxed for six hours at 60-65 C. The reaction solution produced two layers, the top layer being slightly yellow with a darker, oil-like substance on the bottom. The two layers were separated and the darker oil (1-pyrenebutyric methyl ester) was kept and dried under vacuum and analyzed with MS. This product was then dissolved into 6 ml 1,3 diaminopropane and refluxed at 130 C for six hours to produce a clear, brown liquid. This solution was then cooled to 0 C and precipitation was forced by addition of cold water. The solid waxy product of 1-pyrenebutanamide (PBA) was then washed with pure water and allowed to dry prior to analysis.

Conjugation of 5-Beta Cholanamide or 1-Pyrenebutanamide to Hyaluronic Acid 100-200 mg of hyaluronic acid-Na was dissolved into 25 ml nanopure water. 5, 10, or 20 wt % of 5BCA or PBA was dissolved into 25 ml N, N dimethylformamide (DMF) under stirring and low heat. 78-154 mmols EDC and NHS were then dissolved into the HLA/nanopure water solution to give a ten-fold molar excess of crosslinking reagents. The 5BCA/DMF or PBA/DMF solution was then slowly added to the HLA/water solution under constant stirring and the solution was allowed to stir for 24-36 hours. This solution was then dialyzed against 1:1 MeOH:nanopure H$_2$O for 1 day and 100% nanopure for two days using 3500 MWCO dialysis tubing (Fisherbrand, Fisher Scientific). The product was then lyophilized to obtain pure conjugated polymer.

Conjugation of Octadecylamine to HLA

Octadecylamine (ODA) (Sigma Aldrich) was dissolved into a 70% solution of EtOH/H2O. 100 mg 10-20 kDa HLA was dissolved into a separate 70% solution of EtOH/H2O and 78-154 mmols EDC and NHS was then added to give a ten-fold molar excess. The ODA solution was then added slowly into the HLA solution under stirring and the reaction was allowed to proceed for 24-36 hrs. This solution was then dialyzed against 1:1 MeOH:nanopure H2O for 1 day and 100% nanopure for two days using 3500 MWCO dialysis tubing.

ICG Loading into Nanoparticles

HLA-ligand was dissolved into 5 ml nanopure water. 20 wt % ICG was then dissolved in 5 ml DMSO and added to HLA/water solution. This solution was vortexed and then dialyzed against pure water for 24-36 hours using 3500 MWCO dialysis tubing. The product was then filtered through PD-10 columns (GE Lifesciences) to remove free ICG. This product was then lyophilized to obtain the final ICG loaded nanoparticle material.

Nanoparticle Characterization

Lyophilized ICG(+) or ICG(−) NPs were dissolved in nanopure water and filtered through a 0.45 um filter. This solution was then analyzed by dynamic light scattering (DLS) (Brookhaven, ZetaPlus), absorption spectroscopy (Shimadzu, UV-2600), and fluorescence spectroscopy (Horiba Scientific, Fluoromax-4). ICG-loading content was determined with absorbance spectroscopy.

NPs will be resuspended from lyophilized powder in nanopure 18.2 MΩ water to a concentration of 0.1 mg/ml. Prior to spectroscopic measurements, NPs will be confirmed by DLS and any large aggregates will be removed with a 450 μm syringe filter. The extinction spectra will be collected from 500-900) nm. Fluorescence spectra are examined using $\lambda ex=750$ nm and $\lambda em=790-950$ nm, in 1 nm increments, and integration time=0.1 s. To the nanoparticle solution will be added an equal volume of either DMSO or FBS. Release of loaded dye into DMSO will be used for quality assurance, while activation in FBS will indicate nonspecific interaction.

Absorbance and emission properties will then be tested. Serum or albumin can be used but serum may be preferred relative to albumin alone as ICG associates with several serum proteins, primary lipoproteins and serum. fHNPs that show high stability in serum (as determined by a scattered ICG extinction spectra and quenched fluorescence) will undergo further studies for specific nanoparticle degradation and fluorescence activation. For consistency, fluorescence activation studies will be performed at 37° C. in a heating block. Nanoparticle (0.1 mg/ml) suspended in 10% serum will be incubated with 200 units of HYAL-1 (Sigma-Aldrich) in buffer at pH 7.2 and 5.0 to simulate extracellular and intracellular conditions, respectively. Controls will include incubation with pH 7.2 and 5.0 buffer alone and with a HYAL inhibitor, e.g. Methyl indole-3-carboxylate or 6-palmitoyl-Lascorbic acid. At specific time points, aliquots of the mixture will be immediately placed on ice, fluorescence and absorbance spectra will be obtained, and the mixture will be subjected to SEC with multiple detectors to monitor fHNP degradation. NPs are optimized to minimize nonspecific activation and, in turn, the degradation rate of the NPs may affect fluorescence activation kinetics. Thus, a fluorescence activation experiment will be performed over 72 hours, with analysis at 0, 5, 10, 15, 30, and 60 min and 2, 4, 8, 24, 36, 48, and 72 h of incubation time.

In Vitro NP Uptake

MDA-MB-231 cells were incubated for 24 hours in media containing 1 mg/ml 5% PBA-HLA NPs on chamber slides. Cells were then washed repeatedly with PBS to remove free NPs and ICG, then stained with DAPI and imaged using a microscope equipped with NIR filter and camera set.

In Vitro Fluorescence Enhancement.

fHNPs are uptaken by CD44 expressing tumor cells. Fluorescence activation specificity will be evaluated, which includes targeting, intracellular distribution, kinetics, and overall intensity of novel fHNPs in vitro. MDA-MB-231 cells will be plated onto chamber slides. After adhering overnight, cells will then be incubated for up to 24 hours in serum-free RPMI-1640 media containing 0.5-1 mg/ml of ICG or Cy7.5 loaded/conjugated HLA-based NPs. After incubation, cells will be washed three times with PBS to remove free NPs and NIR fluorescent dye. Cell nuclei will be stained with DAPI and imaged using an Olympus X63 microscope equipped with Xenon light source CRi Nuance Ex Camera and NIR filter, both light source and detector are optimized for NIR imaging. Images will then be quantified. Controls will include: free dye, incubation at 4° C. to inhibit endocytosis, adding an excess of HYAL-1 in the culture media (to confirm that NPs do indeed need to be intact to deliver NIR fluorophore to CD44+ cells), and/or a HYAL-1 inhibitor.

HLA mediated delivery of ICG does result in a punctate fluorescence distribution of ICG. Assays will be performed with commercially available kits that specifically label endosomes and lysosomes to detect colocalization of NIR fluorophores with endo/lysosomes.

Cytotoxicity

MDA-MB-231 cells were seeded into 96 well plates and allowed to adhere for 24 hours. Cells were then mixed with media containing 5% 5-βCA-HLA NPs, ICG-loaded 5% 5-βCA-HLA NPs, or ICG alone at concentrations from 0.0005 mg/ml to 1 mg/ml for NPs or 0.0001 to 0.2 mg/ml for ICG. Cells were incubated for 24 hours followed by analysis with the metabolic CCK-8 (Cell Counting Kit-8, Sigma Aldrich) assay.

In Vivo Testing

Twelve to fourteen week old female nude mice (Jackson Labs) were injected subcutaneously with $2 \times 10^6$) MDA-MB-231 cells in 50/50 media/matrigel. MDA-MB-231 cells were transfected with NIR fluorescent protein (iRFP). When the tumors reached 500-1000 mm$^3$, 10 nmol ICG or fHNP (10 wt % PBA was the hydrophobic ligand in this case) was injected into a tail vein. After 24 hours the mice were euthanized and imaged whole using a LI-COR Pearl Impulse system, which has a "700 nm" channel that can detect iRFP-labeled cell and an "800 nm" channel that can detect ICG or Cy7.5. Mice then underwent image-guided tumor removal with the fluorescence image-guided surgical system method. First, skin was removed to expose the breast tumor xenograft. FIG. 9 is indicative of fHNP clearly identified tumor in the fluorescence image-guided surgical system method including, debulking, and positive margin detection. Mice were then re-imaged on the LI-COR system to compare area identified as tumor by the fluorescence image-guided surgical system with iRFP labeled tumors. This was followed by necropsy, further image acquisition for the overall estimation of relative ICG biodistribution, and preparation of tissues for histology. Analysis of the relative biodistribution indicated that ICG delivered by HLA-based nanoparticles is predominantly uptaken by tumor and liver, and kidneys (to a much lesser degree), which is consistent with the biodistribution profile of free ICG.

Fluorescence activation due to enzymatic degradation of HLA with HYAL-1 will be characterized with various cancer cell lines (e.g. CaP). The NPs will be tested in vivo in mice bearing DU145 and LNCaP xenografts to compare fHNP contrast agents and ICG for optimized tumor enhancement.

The chemical composition of fHLA will also be modified for loading of the lipophilic FAS inhibitor, Orlistat, yielding fHNP-Orl NPs that will be capable of therapy and imaging. Controlled Orlistat release due to the presence and absence of HYAL-1 will be measured in biochemical and in vitro experiments using CaP cell lines. An in vivo study will be performed on human CaP tumor xenografts in mice. The effect of tumor inhibition of fHNP-Orl and Orlistat alone will be compared.

Efficacy of Fluorescence Enhancement in Mice and Ability to Minimize Tumorrecurrence.

In one embodiment, the present invention relates to the evaluation of tumor contrast enhancement by NIR fluorescent HLA-based nanoparticles in mice bearing human breast tumor xenografts. NIR fluorophores are ideal for image-guided surgery because of the minimal absorbance and scattering of endogenous tissue at wavelengths in the biologically clear window (700-1000 nm) (21). Additionally, the present invention relates to using highly sensitive optical imaging instrumentation to detect these agents at relatively low-cost. The methods employed herein will also be quite amenable to bringing into the operating room. The present invention also relates to specifically targeted NIR fluorescent nanoparticles using the fluorescence image-guided surgical system method to effect complete tumor removal.

Accordingly, the present invention relates to being able to ascertain and/or demonstrate: (1) the dynamic contrast enhancement pattern of NIR fluorescent NPs compared to free NIR dye and identifying the (2) NIR fluorescent NPs with the highest contrast enhancement and test them for their efficacy to effect complete removal of an entire tumor. In one embodiment, the NIR fluorophore delivered to tumors via HNPs, specifically CD44+ tumors, will provide brighter and more sustained tumor enhancement than free dye. The combination of specific targeting and stronger tumor signal will yield tumor margins that are visible by the fluorescence image-guided surgical system method, resulting in decreased tumor recurrence. The present invention relates to data that shows fHNP provides significantly stronger contrast in tumors than free ICG. In an embodiment, the present invention uses the human breast tumor cell line, MDA-MB-231 to form xenografts in nude mice. NIR fluorescent NPs will be systemically injected and tumor localization will be monitored by either whole animal fluorescence imaging over time or with fluorescence image-guided surgical system method, which is described herein. The efficacy of the instant novel nanoparticles compared to control agents will be evaluated by comparing signal intensity data in tumors compared to other tissues, detectability by the fluorescence image-guided surgical system method, histopathology to quantify the relationship between the presence of tumor tissue and NIR signal, and overall tumor recurrence.

Contrast-Enhancement Dynamics of NIR Fluorescent Ni's in a Breast Tumor Model.

Female athymic nude mice aged 8-12 weeks will have MDA-MB-231 tumor cells injected subcutaneously into a flank. iRFP-labeled MDA-MB-231 cells will be used to aid co-localization of tumor cells and contrast agent. When tumors reach 500 mm$^3$, approximately 3-5 weeks after injection, a NIR fluorescent NP or free dye will be administered via a tail vein. NP dose will be normalized based on ICG; and using a dose of about 0.357 mg/kg ICG provides significant tumor enhancement. NIR fluorescence signal will be imaged at 800 nm using a Pearl Impulse Small Animal imaging System (LI-COR Biosciences) at pre-injection at times 0.5, 1, 4, 8, 24, 48, and 72 h after injection. Signal in tumor relative to surrounding tissue will be measured at each time point.

The maximum spatial resolution of the LI-COR is 85 μm and thus cannot evaluate the cellular level distribution of agents. Therefore, groups of mice will be euthanized at 4, 24, and 72 h and necropsied. A detailed histological analysis will be performed on the tumor and surrounding tissue to accurately characterize the distribution of HLA-based contrast agent in the tumor and associated stroma. Detailed blood pharmacokinetic and biodistribution experiments will be performed in healthy mice as part of the imaging agent safety evaluation).

Efficacy of NIR Fluorescent NPs for Image-Guided Surgery.

Using mice bearing human breast tumor xenografts, the efficacy of the newly synthesized NIR fluorescent nanoparticles for IGS will be determined. MDA-MB-231-iRFP cells ($2\times10^6$) will be injected into the flank of female nude mice aged 8-12 weeks and will be allowed to grow until they reach approximately 500-1000 mm$^3$, at which point these tumors can invade into surrounding tissue. Mice will then have one of 3-4 nanoparticle formulations that provided the strongest contrast enhancement. Free NIR dye and a sham saline injection will serve as controls. Mice will then undergo IGS with the fluorescence image-guided surgical system method to remove any fluorescently enhancing tumor tissue due to nanoparticle or control dye. The sham control groups will also undergo image-guided surgery to account for any effect due to autofluorescence—however, NIR autofluorescence is not expected to contribute at 800 nm—and standard surgery with only visual and tactile cues. Consistent imaging system parameters will be used between different experimental groups. Consistent surgical technique will also be used. After surgery, the mice will be allowed to recover and tumor recurrence will be monitored weekly in the iRFP (700 nm) channel of the LI-COR imaging system for 28 days or when a mouse is scheduled for euthanasia due to tumor burden or associated morbidity. After euthanasia, mice will be necropsied and tumor burden will be measured by three methods per contrast agent, control, or sham. First, the number of palpable tumors will be measured for each group. Second, a 1 cm$^2$ area from where the primary tumor was removed will have 4-6 tissue samples taken in that area and undergo histological examination. 5 fields at 20× in each tissue sample will be examined for the presence of tumor (either by H&E or by iRFP fluorescence). Tumor recurrence in this case would be quantified by number of tumor-positive fields per mouse. Third, adjacent lymph nodes, liver, lung, brain and bone will first undergo LI-COR imaging to detect metastatic iRFP-labeled breast tumor cells and then 3-5 representative histological sections per organ per mouse will be inspected for tumor presence. Quantification will include determining the number of measured metastatic sites per mouse.

fHNPs will produce stronger tumor enhancement relative to surrounding tissue when compared to a free dye control. fHNPs used will be selected based on minimized serum protein interaction and specific controlled release due to HYAL-1 degradation of the NP. The chemical modifications used to achieve this, such as chemical crosslinking and PEGylation could effect, blood pool circulation times, the rate that the nanoparticles accumulate in tumor, and time until specific activation. Thus, the time to peak fluorescence enhancement could be less, but likely more than the time observed until peak enhancement with a free dye control.

The efficacy of the two lead fHNPs for image-guided surgery in a murine xenograft model will be evaluated. MDAMB-231-iRFP tumors will be grown until they are 500-100 mm$^3$ in size. Imaging agents will be injected systemically and IGS will be performed at maximal fluorescence contrast as determined a time-dependent enhancement study. The primary tumor will be removed to the point where no fluorescence enhancement is observed using the fluorescence image-guided surgical system method. The surgical cavity will then be harvested and be examined for the presence of tumor cell deposits using IHC. The efficacy of fHNPs compared to free dye or a sham control will be quantified by the number of tumor deposits left in the surgical cavity after IGS is performed.

In an alternative embodiment, each tumor (whether or not fHNP or control dye has been administered) will be removed without image-guidance, only by normal visualization and touch. An image with the image-guided surgery system will then be obtained. Then 3-5 sections of the margin will be harvested and the level of fluorescence remaining in the imaging system will be compared to the number of positive tumor fields. In this case, the number positive field is likely to remain consistent because the tumor will be removed without image guidance. Fluorescence remaining will be due to targeting and activation of the nanoparticle compared to the nonspecific accumulation of control.

Biodistribution of Hyaluronic Acid Derived Nanoparticle Intraoperative Imaging Agents.

The biodistribution and elimination of fHNP and control dyes will be tested in CD-1 mice. Each mouse will receive an intravenous dose of 500 µg-fluorophore/kg equivalent via a tail vein. At 1, 4, and 10 days, mice will be euthanized by $CO_2$ asphyxiation followed by cervical dislocation. Organ and tissue samples from the blood, liver, kidneys, spleen, heart, skeletal muscle, fat, lungs, stomach, small and large intestines, brain, femur, and lymph will be excised and weighed. All tissues will be homogenized in an equal volume (based on weight) of PBS. Each homogenate will be extracted with AN:MeOH (47:3), vortexed, centrifuged, filtered, and undergo spectrophotometric quantification of the NIR dye. The femur will be dissolved overnight in nitric acid and then undergo the same extraction method and dye quantification.

It is expected that nanoparticle formulations of NIR dyes will not induce necrosis or apoptosis. This is consistent with NP formulations based on HLA with multiple fluorophores that have been directly conjugated. HLA itself does not induce an immune or inflammatory response and has anti-inflammatory properties.

In one embodiment, HPLC methods can be used to precisely quantify the level of parent ICG. Changes due to polymeric nanoparticle formulation and chemical conjugation NIR dyes will undergo HPLC analysis in the first three mice/rats of the in vive biodistribution and/or pharmacokinetic studies to determine if there is a significant difference between NIR dye amount by spectroscopy and HPLC.

In an embodiment, the present invention relates to a composition for detecting cancer comprising one or more nanoparticles, hyaluronic acid, and at least one fluorophore that both absorbs and fluoresces well into a near infrared range. In a variation, the fluorophore is indocyanine green.

In an embodiment, the present invention relates to being able to evaluate intraoperative imaging agents that fluorescently contrast-enhance various cancers (such as breast or prostate cancer) during surgery by image-guided surgical instrumentation giving physicians more effective visualization of the cancer, thereby increasing the probability of complete tumor removal. In one embodiment, the present invention relates to HLA-based NPs that entrap the NIR fluorophore, ICG. In an embodiment, the present invention relates to fluorescent HLA-based NPs that entrap the fatty acid synthase (FAS) inhibitor, Orlistat, and specifically deliver it to the cancer site for neoadjuvant therapy to image-guided surgery.

In an embodiment, the composition of the one or more nanoparticles may be self-assembled. In an embodiment, the composition may self-assemble by being aided by use of one or more of 5-β cholanic acid, 1-pyrenebutyric acid or octadecylamine. In an embodiment, the present invention relates to these polymers that assemble into nanoparticles both with and without ICG.

In addition to the various cancers that the composition of the present invention may be used to detect, the composition may also detect cancers that are one or more members selected from the group consisting of breast cancer, ovarian cancer, and prostate cancer.

The composition of the present invention may have one or more nanoparticles that contain hyaluronic acid as part of the one or more nanoparticles.

The composition may further comprise one or more of 5-beta cholanamide or 1-pyrenebutanamide. In one variation, the hyaluronic acid may be cross-linked to at least one of the one or more 5-beta cholanamide or 1-pyrenebutanamide.

In an embodiment, the composition may comprise polyethylene glycol (PEG), which has been shown to decrease nonspecific protein interaction. This can result in increased blood circulation times, but in this case may also prevent nonspecific NIR fluorescence activation. In one embodiment, amine functionalized PEG (mw=2000 Da; Rapp Polymere, Tübingen, Germany) will be grafted to the carboxyl groups of HLA The studies to date that have been done indicate that PEG (mw=550-2000 Da) added to biodegradable paramagnetic contrast agents greatly increases plasma half-life of the agents.

The composition may further comprise one or more fatty acid synthase inhibitors. The one or more fatty acid synthase inhibitors may be one or more members selected from the group consisting of Cerulenin, Quercetin Dihydrate, Kaempferol, C75 (4-Methylene-2-octyl-5-oxotetrahydrofuran-3-carboxylic acid), Luteolin, BML-275 (Dorsomorphin), Pyrazinamide, Platensimycin, Lipase Inhibitor THL (Orlistat), and Triclosan.

The composition may further contain anticancer agents.

In an embodiment, the present invention relates to methods of using the composition for detection of cancer. In one embodiment, the method may be used for detecting a cancerous growth either pre-clinically using in-vivo models, or clinically by mapping sentinel lymph nodes. The method can use the composition for detection in breast cancer, skin cancer, GI cancer, lung cancer, or prostate cancer using intraoperative fluorescent imaging of a composition that comprises one or more nanoparticles, hyaluronic acid, and at least one fluorophore that both absorbs and fluoresces in a near infrared range.

In one aspect, the method uses a composition wherein the fluorophore is indocyanine green.

In one embodiment, the method uses a composition wherein the one or more nanoparticles are self-assembled. In one embodiment, self-assembly may be aided by use of one or more of 5-β cholanic acid, 1-pyrenebutyric acid or octadecylamine.

The method may be used for cancer as disclosed above or alternatively, may be used against one or more members selected from the group consisting of breast cancer, ovarian cancer, and prostate cancer.

In an embodiment, the composition and the methods of using the composition ideally provide one or more of the following optimized parameters: colloidal stability, fluorescence activation specificity, in vivo contrast enhancement and/or minimal toxicity.

In an embodiment, the method may use one or more nanoparticles that contain hyaluronic acid as part of the one or more nanoparticles.

In a variation, the method may employ a composition that further comprises one or more of 5-beta cholanamide or 1-pyrenebutanamide. In one embodiment, the hyaluronic acid may be cross-linked to at least one of the one or more of 5-beta cholanamide or 1-pyrenebutanamide.

In one variation, the method may employ a composition that further comprises one or more fatty acid synthase inhibitors. In one embodiment, the one or more fatty acid synthase inhibitors may be one or more members selected from the group consisting of Cerulenin, Quercetin Dihydrate, Kaempferol, C75 (4-Methylene-2-octyl-5-oxotetrahydrofuran-3-carboxylic acid), Luteolin, BML-275 (Dorsomorphin), Pyrazinamide, Platensimycin, Lipase Inhibitor THL (Orlistat), and Triclosan.

In a variation, the present invention relates to pharmaceutical compositions and methods using those pharmaceutical compositions. The pharmaceutical composition may contain pharmaceutically acceptable salts, solvates, and prodrugs thereof, and may contain diluents, excipients, carriers, or other substances necessary to increase the bioavailability or extend the lifetime of the compounds and/or compositions of the present invention.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of cancer treatment.

The pharmaceutical compositions containing a compound of the invention may be in a form suitable for injection either by itself or alternatively, using liposomes, micelles, and/or nanospheres.

In an embodiment, the compositions of the present invention may be used as injectables. The composition intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate.

The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising the conjugate(s) or compositions as described herein or a salt thereof.

A solution of the invention may be provided in a sealed container, especially one made of glass, either in a unit dosage form or in a multiple dosage form.

Any pharmaceutically acceptable salt of a compound of the conjugate(s) as described herein may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the conjugate(s) as described herein is a hydrochloric acid salt including a mono, di, or trihydrochloride.

Any solvent which is pharmaceutically acceptable and which is able to dissolve the conjugate(s) as described herein or a pharmaceutically acceptable salt thereof may be used. The solution of the invention may also contain one or more additional components such as a co-solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

Suitable solvents and co-solubilizing agents may include, but are not limited to, water, sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise the conjugate(s) as described herein or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the conjugate(s) as described herein or a pharmaceutically acceptable salt thereof may be less than 100 mg/mL, or less than 50 mg/mL, or less than 10 mg/mL, or less than 10 mg/mL and greater than 0.01 mg/mL, or between 0.5 mg/mL and 5 mg/mL, or between 1 mg/mL and 3 mg/mL. In an embodiment, the concentration that is used is the ideal concentration to be used for identification purposes and/or to be sufficiently cytotoxic to the cancer cells yet limit the toxicity on other cells.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising the conjugate(s) and/or compositions as described herein or a pharmaceutically acceptable salt thereof in a physiologically acceptable solvent, and which has a pH of from 2.5 to 3.5. For solution formulations, various compounds and/or compositions of the present invention may be more soluble or stable for longer periods in solutions at a pH lower than 6. Further, acid salts of the compounds and/or compositions of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving the conjugate(s) as described herein or a pharmaceutically acceptable salt thereof in a pharmaceutically acceptable solvent. Where a pharmaceutically acceptable acid salt of the conjugate(s) as described herein is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

One or more additional components such as co-solubilizing agents, tonicity adjustment agents, stabilizing agents and preservatives, for instance of the kind previously specified, may be added to the solution prior to passing the solution through the sterilizing filter.

In a further variation, the present invention contemplates combination therapies in which the compounds and/or compositions of the present invention can be used in conjunction with other the compositions of the present invention. It is also contemplated and therefore within the scope of the invention that other anti-neoplastic agents/compounds can be used in conjunction with the compounds and/or compositions of the present invention. The anti-neoplastic agents/compounds that can be used with the compounds and/or compositions of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds and/or compositions of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds and/or compositions of the present invention include Campath, IL-8, B-FGF, Tek antagonists, anti-TWEAK agents (e.g., specifically binding antibodies or antigen binding regions, or soluble TWEAK receptor antagonists, ADAM distintegrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other anti-angiogenic/anti-tumor agents that can be used in conjunction with the compounds and/or compositions of the present invention include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA); ilomastat, (Arriva, USA); emaxanib, (Pfizer, USA,); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland); the ARGENT technology of Ariad, USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142, (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and Medimmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, genebased, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University. USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery. Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YHI6, (Yantai Rongchang, China); S-3APG, (Boston Children's Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI4610, (Sima, USA); heparanase inhibitors, (InSight, Israel): KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

It is contemplated and therefore within the scope of the invention that the compounds and/or compositions of the present invention can be modified to target specific receptors or cancer cells or can be modified so that they can survive various in vim environments. In a variation, the conjugates, compositions, and methods of the present invention can be used against solid tumors, cell lines, and cell line tissue that demonstrate upregulated nucleotide excision repair and other upregulated resistance mechanisms.

It is contemplated and therefore within the scope of the present invention that any feature that is described above can be combined with any other feature that is described above. Further, it is contemplated and therefore within the scope of the invention that any feature can be omitted that is described can be omitted. When conjugates and/or compositions are discussed, it should be understood that those conjugates and/or compositions are contemplated as being parts of methods of identifying tumors, methods of treatment and/or methods of making. Moreover, it should be understood that the present invention contemplates minor modifications that can be made to the compounds, conjugates, compositions and methods of the present invention. In any event, the present invention is defined by the below claims.

We claim:

1. A composition for detecting cancer comprising one or more nanoparticles comprising hyaluronic acid and at least one fluorophore that both absorbs and fluoresces well into a near infrared range, wherein the at least one fluorophore is physically entrapped in the one or more nanoparticles, wherein the hyaluronic acid is chemically conjugated to 1-pyrenebutanamide, wherein the one or more nanoparticles are less than 160 nm in diameter prior to loading the at least one fluorophore, wherein the one or more nanoparticles have a diameter ranging from about 79 nm to about 90 nm.

2. The composition of claim 1, wherein the fluorophore is indocyanine green.

3. The composition of claim 1, wherein the one or more nanoparticles is self-assembled.

4. The composition of claim 1, wherein the cancer is one or more members selected from the group consisting of breast cancer, ovarian cancer, and prostate cancer.

5. A method of detecting cancerous growth in a subject, comprising administering to the subject the composition of claim 1 and using intraoperative fluorescent imaging of the composition to detect cancerous growth in the subject.

6. The method of claim 5, wherein the fluorophore is indocyanine green.

7. The method of claim 5, wherein the one or more nanoparticles is self-assembled.

8. The method of claim 5, wherein the solid tumor is a cancer selected from the group consisting of breast cancer, ovarian cancer, skin cancer, GI cancer, lung cancer and prostate cancer.

9. The composition of claim 1, wherein the 1-pyrenebutanamide has a loading ratio ranging from 5 mol % to 10 mol % relative to hyaluronic acid.

10. The composition of claim 1, wherein the one or more nanoparticles have a diameter of about 79 nm.

11. The composition of claim 1, wherein the nanoparticles have a fluorophore loading efficiency of about 0.5.

* * * * *